(12) United States Patent
Heck

(10) Patent No.: US 9,393,382 B2
(45) Date of Patent: Jul. 19, 2016

(54) HIGH-FLOW TAPERED PERIPHERAL IV CATHETER WITH SIDE OUTLETS

(75) Inventor: Robert W. Heck, Park City, UT (US)

(73) Assignee: Robert W. Heck, Park City, UT (US)

(*) Notice: Subject to any disclaimer, the term of this patent is extended or adjusted under 35 U.S.C. 154(b) by 1640 days.

(21) Appl. No.: 12/717,766

(22) Filed: Mar. 4, 2010

(65) Prior Publication Data

US 2010/0286657 A1 Nov. 11, 2010

Related U.S. Application Data

(60) Provisional application No. 61/175,672, filed on May 5, 2009.

(51) Int. Cl.
| | | |
|---|---|---|
| *A61M 25/06* | (2006.01) | |
| *A61M 25/00* | (2006.01) | |
| *A61M 25/01* | (2006.01) | |
| *A61M 29/00* | (2006.01) | |

(52) U.S. Cl.
CPC ....... *A61M 25/0606* (2013.01); *A61M 25/0023* (2013.01); *A61M 25/0102* (2013.01); *A61M 25/007* (2013.01); *A61M 29/00* (2013.01)

(58) Field of Classification Search
CPC ............ A61M 25/00; A61M 25/0023; A61M 25/007; A61M 25/0102; A61M 25/0606
USPC ............... 604/506, 507, 508, 510, 164.01, 604/164.06, 164.13, 166.01, 167.01, 604/170.01, 170.02, 170.03, 264, 272, 523, 604/525, 284

See application file for complete search history.

(56) References Cited

U.S. PATENT DOCUMENTS

| | | | |
|---|---|---|---|
| 3,570,485 A | | 3/1971 | Reilly |
| 3,670,729 A | * | 6/1972 | Bennett et al. ................ 604/500 |
| 3,924,633 A | | 12/1975 | Cook et al. |
| 4,099,528 A | | 7/1978 | Sorenson et al. |
| 4,177,809 A | | 12/1979 | Moorehead |
| 4,405,314 A | | 9/1983 | Cope |
| 4,531,935 A | | 7/1985 | Berryessa |
| 4,808,158 A | | 2/1989 | Kreuzer et al. |
| 4,977,897 A | | 12/1990 | Hurwitz |
| 5,002,535 A | * | 3/1991 | Gross ............................ 604/272 |
| 5,147,334 A | | 9/1992 | Moss |
| 5,330,433 A | * | 7/1994 | Fonger et al. ................. 604/500 |

(Continued)

OTHER PUBLICATIONS

Soo, Myung et al., "Splenoportography with multiple sidehole catheter," Oct. 1973, pp. 433-436, vol. 119, No. 2.

(Continued)

*Primary Examiner* — Kami A Bosworth
(74) *Attorney, Agent, or Firm* — Thorpe North & Western, LLP

(57) ABSTRACT

A high-volume peripheral intravenous (IV) catheter and method includes an elongate stylet removably disposed in the lumen of an elongate catheter with the stylet having a beveled distal end forming a piercing tip that protrudes from the outlet port of the catheter. The catheter has a proximal cylindrical shape from the inlet port transitioning at a transition to an inner lumen conical taper terminating at the outlet port, and having a larger internal diameter at the inlet port and a tapering smaller internal diameter between the transition and the outlet port. A plurality of side outlet ports is formed laterally through the catheter in the inner lumen conical taper. A cross-sectional area of the outlet port and the side outlet ports together is equal or greater than a cross-sectional area of the inlet port.

25 Claims, 4 Drawing Sheets

(56) References Cited

U.S. PATENT DOCUMENTS

| | | |
|---|---|---|
| 5,364,374 A | 11/1994 | Morrison et al. |
| 5,643,226 A | 7/1997 | Cosgrove et al. |
| 5,899,890 A * | 5/1999 | Chiang et al. ............... 604/264 |
| 6,102,903 A * | 8/2000 | Tremulis ...................... 604/500 |
| 6,440,119 B1 | 8/2002 | Nakada et al. |
| 6,569,129 B1 * | 5/2003 | Holmes et al. ............... 604/264 |
| 6,595,966 B2 | 7/2003 | Davey et al. |
| 6,676,643 B2 | 1/2004 | Brushey |
| 6,692,473 B2 | 2/2004 | St. Cyr et al. |
| 7,252,653 B2 | 8/2007 | Ueda et al. |
| 7,252,654 B2 | 8/2007 | Van Tassel et al. |
| 7,833,201 B2 | 11/2010 | Carlyon et al. |
| 2006/0189959 A1 | 8/2006 | Schneiter |
| 2007/0100299 A1 * | 5/2007 | Magnusson ................... 604/264 |
| 2008/0195034 A1 | 8/2008 | Hafer et al. |
| 2010/0286657 A1 | 11/2010 | Heck |

OTHER PUBLICATIONS

PCT Application PCT/US2011/026677; filed Mar. 1, 2011; Robert Heck; International Search Report mailed Nov. 15, 2011.

* cited by examiner

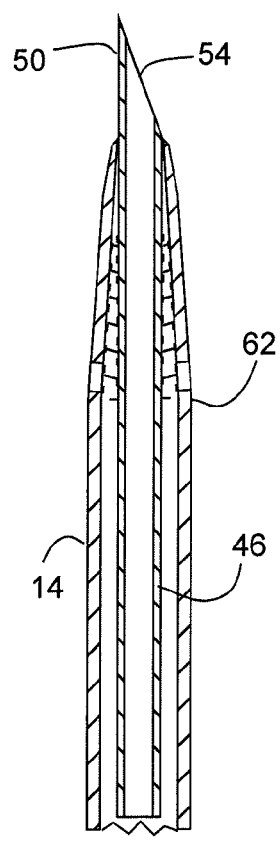
Fig. 7
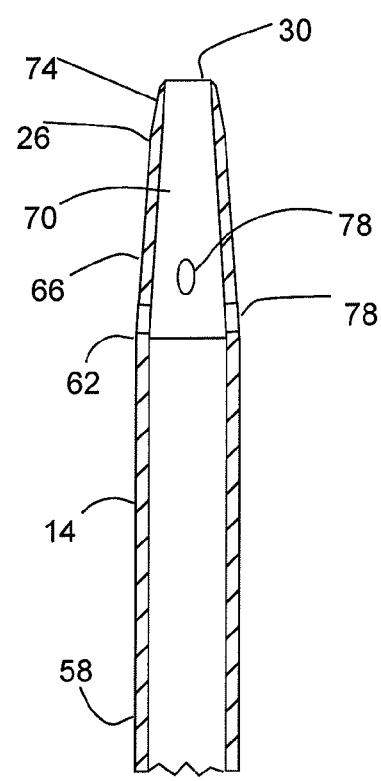
Fig. 8
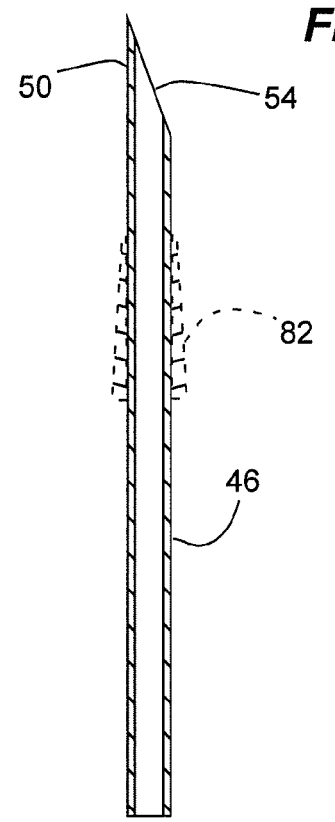

HIGH-FLOW TAPERED PERIPHERAL IV CATHETER WITH SIDE OUTLETS

PRIORITY CLAIM

Priority is claimed to U.S. Provisional Patent Application Ser. No. 61/175,672, filed May 5, 2009, which is hereby incorporated herein by reference in its entirety.

BACKGROUND

1. Field of the Invention

The present invention relates generally to peripheral intravenous (IV) catheters.

2. Related Art

Certain patients require a relatively large amount of fluid to be injected into a vein over a short period of time, and thus require a large bore IV catheter (such as 18 gauge). Examples include surgical patients, septic patients, hemorrhaging patients, trauma patients, dehydrated patients, and those patients needing IV contrast for procedures. For example, CT scans can require that 80 cc bolus of contrast be delivered at a rate of 5 cc/sec through an 18 gauge IV catheter between the patients elbow and wrist. The use of a smaller IV catheter, such as less than 20 gauge, causes the IV tubing to split because the pressure is too high at the connection between the tubing and the IV catheter. A failed CT scan such as this results in wasted time, expense, and excessive radiation exposure to the patient. Some patients, however, have small and/or fragile veins, into which only a small bore IV (such as 22-27 gauge) can be inserted. An inordinate amount of time can be spent trying to insert a large catheter into the small or fragile vein, and often this large catheter damages the vein yielding a failed IV attempt. Multiple IV insertion attempts are painful to the patient, time consuming and frustrating for the technician, and expensive for the facility.

SUMMARY OF THE INVENTION

It has been recognized that it would be advantageous to develop a device and method for introducing high velocity and high volume liquids, such as contrast or blood, into a vein at low pressure. In addition, it has been recognized that it would be advantageous to develop a device and method with a large bore inlet and small bore outlet. Furthermore, it has been recognized that it would be advantageous to develop a device and method that combines the ease of inserting a small bore IV catheter into a vein with the flow and low pressure of a large bore IV catheter.

The invention provides a high-velocity, high-volume peripheral intravenous (IV) catheter device with an elongate catheter having an elongate lumen therein, an inlet port at a proximal end, and an outlet port at a distal end opposite the inlet port. The catheter can have a length between 1-3 inches. The lumen has a proximal cylindrical shape from the inlet port transitioning at a transition to a distal tapered conical shape terminating at the outlet port, and defining an inner lumen conical taper at the distal end thereof. The lumen has a larger internal diameter at the inlet port and a tapering smaller internal diameter between the transition and the outlet port. The larger internal diameter at the inlet port of the lumen can be 16-18 gauge. A smaller internal diameter of the outlet port can be 20-27 gauge. A plurality of side outlet ports is formed laterally through the catheter. A cross-sectional area of the outlet port and the side outlet ports together are equal or greater than a cross-sectional area of the inlet port. A hub is disposed at the inlet port of the catheter.

In accordance with a more detailed aspect of the present invention, the plurality of side outlet ports can be formed through the inner lumen conical taper of the catheter. In addition, the plurality of side outlet ports can be located nearer the transition that the outlet port.

In accordance with a more detailed aspect of the present invention, the catheter device can include an elongate stylet removably disposed in the lumen of the catheter and insertable and removable through the hub and the inlet port. The stylet can have a beveled distal end forming a piercing tip that protrudes from the outlet port of the catheter when the stylet is completely inserted in the catheter.

In addition, the invention provides a method for high-velocity, high-volume peripheral intravenous (IV) introduction of a liquid into a vein with a catheter device. The method includes piercing a patient's skin and vein wall with the piercing tip of the elongate stylet completely inserted into the catheter. The distal end of the catheter is advanced along with the stylet through the patient's skin and vein wall along the vein. The distal tapered conical shape of the catheter is advanced through the patient's skin and vein wall along the vein to position the plurality of side outlet ports in the vein. The stylet is withdrawn from the lumen of the catheter. Tubing or a syringe is coupled to the hub at the inlet port of the catheter. A high velocity and high volume liquid is injected into the inlet port of the catheter with the liquid flowing out the plurality of side outlet ports and the outlet port.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 7 is a schematic partial cross-sectional side view of the peripheral IV catheter of FIG. 1;

FIG. 8 is a schematic partial cross-sectional side view of the peripheral IV catheter of FIG. 7, shown with the stylet removed from the catheter.

Figure 1:
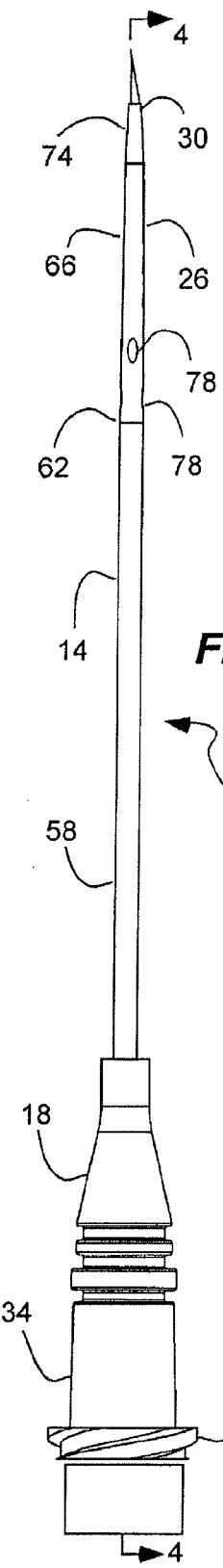
FIG. 1 is a side view of a high-volume peripheral intravenous (IV) catheter in accordance with an embodiment of the present invention.
Figure 2:
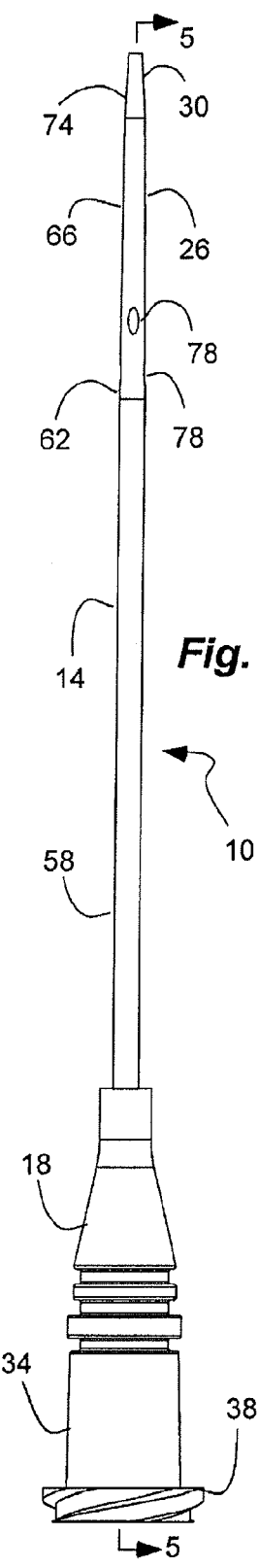
FIG. 2 is a side view of a catheter of the peripheral IV catheter of FIG. 1.
Figure 3:
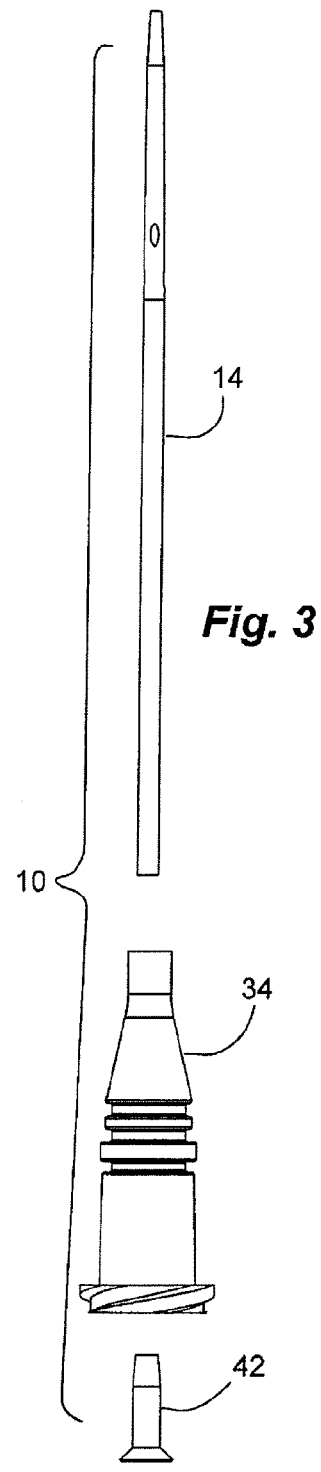
FIG. 3 is an exploded side view of the catheter of FIG. 2.
Figure 4:
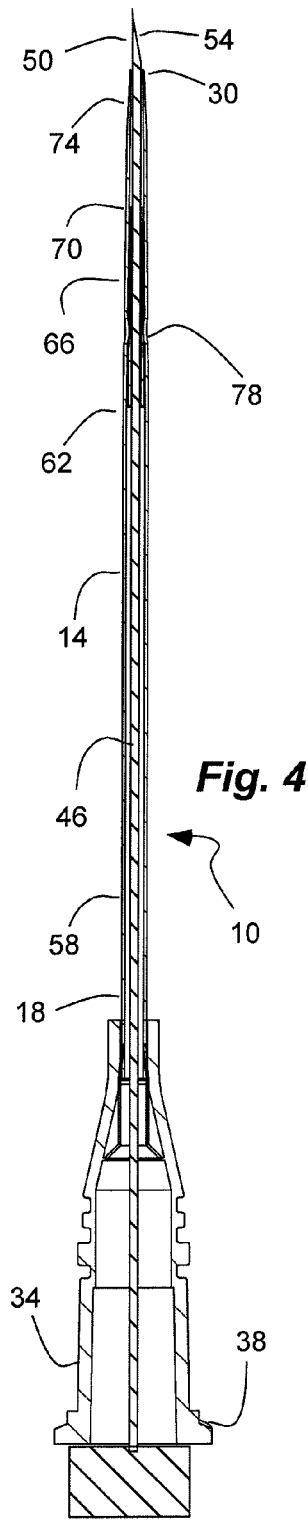
FIG. 4 is a cross-sectional side view of the peripheral IV catheter taken along line 4-4 of FIG. 1.
Figure 5:
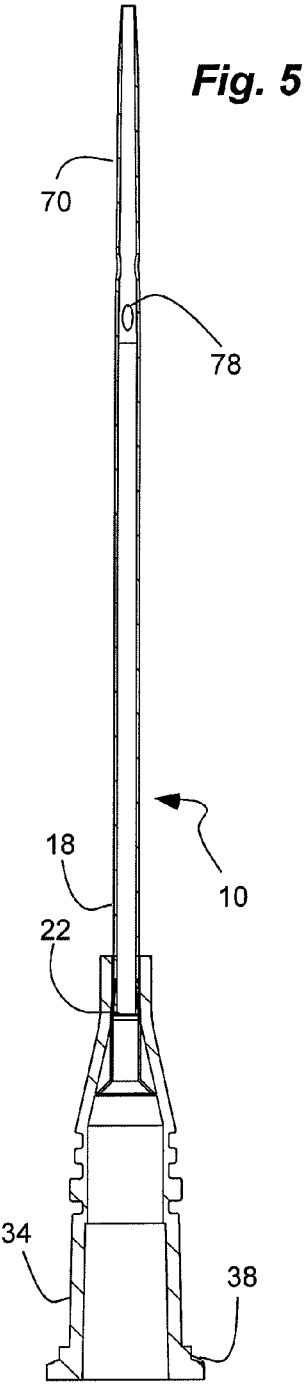
FIG. 5 is a cross-sectional side view of the catheter taken along line 5-5 FIG. 2.
Figure 6:
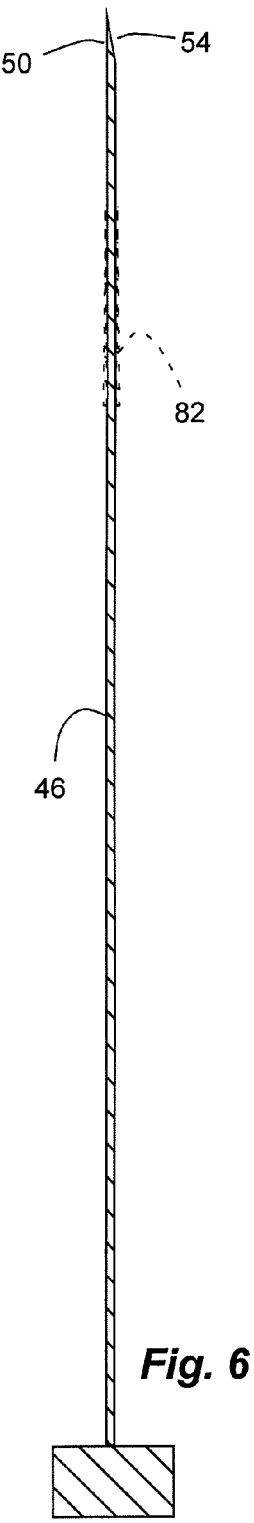
FIG. 6 is a side view of a stylet of the peripheral IV catheter of FIG. 1.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

As illustrated in FIGS. 1-8, a high-volume peripheral intravenous (IV) catheter, indicated generally at 10, in an example implementation in accordance with the invention is shown. Such an IV catheter can be used for introducing a high velocity, high volume fluid into a patient's vein at relatively low inlet and outlet pressures. Such an IV catheter can accommodate a larger inlet, such as 16-18 gauge, and can easily enter a smaller vein, with a 20-27 gauge insertion needle. For example, such an IV catheter can be used to introduce contrast into a patient's vein prior to a CT scan.

The IV catheter 10 includes an elongate catheter 14 with an elongate lumen. The catheter 14 can be flexible and non-compressible. Thus, the catheter can bend and flex with respect to the patient's vein, without compressing and closing off the lumen. The catheter can be flexible enough to bend and flex under its own weight. The catheter can be formed of plastic or the like. The catheter 14 or lumen has a proximal end 18 with an inlet port 22 (FIG. 5) and an opposite distal end 26 with an outlet port 30. The catheter and lumen can have a straight and linear configuration in a relaxed state with a straight and linear longitudinal axis. The inlet and outlet ports 22 and 30 can be opposite or opposing one another and aligned with the straight and linear longitudinal axis in the relaxed state. The catheter 14 can have a length between 1 to 3 inches long. In one aspect, the catheter is approximately 2 inches long. In another aspect, the catheter is approximately 1.15 inches long. The catheter can have a wall thickness of approximately 0.0085 inches thick. The proximal end of the catheter can be 16-18 gauge. For example, for a proximal end of 18 gauge, the outer diameter of the proximal end of the catheter can be approximately 0.050 inches, while the inner diameter of the proximal end can be approximately 0.033 inches.

A hub 34 is coupled to the proximal end 18 of the catheter which can define or form the inlet port 22. The hub 34 can have a connector 38, such as a standard Luer lock connector, for connecting to syringes or tubing. The proximal end 18 of the lumen can be coupled to the hub 34 by a ferrule or compression sleeve 42. The hub and ferrule can be formed of plastic and can be rigid with respect to the catheter.

An elongate stylet 46 is removably disposed in the lumen of the catheter 14, and is insertable and removable through the hub 34 and the inlet port 22. The stylet can be hollow and can be a needle. A distal end 50 of the stylet 46 can be beveled to form a piercing tip 54. The piercing tip 54 is sharp and rigid to pierce or penetrate a patient's skin and vein wall. The stylet 46 has a length so that the piercing tip 54 protrudes from the outlet port 30 of the catheter 14 when the stylet is completely inserted in the catheter. A proximal end of the stylet can be configured to engage the hub so that the distal ends of the stylet and catheter can be inserted into a vein. The stylet can be rigid with respect to the catheter and resists bending or flexing, even under force. The stylet can be formed of stainless steel. The stylet can be approximately 22-27 gauge and can have an outer diameter that substantially matches an inner diameter of the outlet port. The lumen of the catheter and the stylet or needle can be configured to have a snug fit.

As discussed above, the catheter 14 or lumen can be configured to provide high flow and low pressure. The proximal end 18 of the lumen can have a proximal cylindrical shape 58 extending from the inlet port 22 or hub 34 to a transition 62. As described above, the proximal cylindrical shape can be 16-18 gauge with an essentially constant inner and/or outer diameter. The lumen transitions at the transition 62 to a distal tapered conical shape 66 terminating at the outlet port 30. The distal tapered conical shape 66 defines an inner lumen conical taper with a conical internal shape 70 at the distal end 26 of the lumen. The lumen can transition from 16-18 gauge at the inlet port and proximal cylindrical shape, to 20-27 gauge at the outlet port 30. Thus, the lumen has a larger internal diameter at the inlet port, and a tapering smaller internal diameter between the transition 62 and the outlet port 30. The proximal cylindrical shape 58 of the lumen can be approximately $3/4^{th}$ to $2/3^{rd}$ the length of the lumen, while the distal tapered conical shape 66 or the conical internal shape 70 can be approximately $1/4^{th}$ to $1/3^{rd}$ the length of the lumen. The distal tapered conical shape 66 and/or conical internal shape 70 can taper at 1.1 degrees. The catheter 14 can have a primary outer taper corresponding to the distal tapered conical shape of the lumen.

Furthermore, a most distal end of the catheter has a further, secondary outer taper 74 with the wall thickness becoming thinner. The secondary taper can extend approximately the last 1/8 inch at the outlet port. The secondary taper transitions from the catheter to the stylet to facilitate insertion of the catheter into the skin and vein as the catheter follows the stylet into the vein. The secondary outer taper can taper at 5.5 degrees.

One or more side outlet ports 78 are formed laterally through the catheter 14. In one aspect, the plurality of side outlet ports can be formed through the distal tapered conical shape 66 of the catheter. In one aspect, the side outlet ports 78 are located close to the transition or the greatest inner diameter while still being located in the distal tapered conical shape. Thus, the side outlet ports 78 can be located nearer the transition 62 than the outlet port 30. Locating the side outlet ports too close to the outlet port and too far from the transition may reduce the flow benefit; while locating the side outlet ports too far from the outlet port and too close to the inlet may increase the risk of the side outlet ports being outside the vein, leading to infusion of fluid into soft tissue. In one aspect, at least one circumferential row of side ports can be located in the distal tapered conical shape of the lumen where the diameter is greatest to maximize flow. Thus, one or more of the side outlet ports can be positioned in the distal tapered conical shape immediately adjacent or abutting to the transition. Alternatively, one or more of the plurality of side outlet ports can also be disposed in the cylindrical shape 58 of the catheter adjacent or abutting to the transition.

A cross-sectional area of the outlet port 30 and the side outlet ports 78 together are equal to or greater than a cross-sectional area of the inlet port 22. Thus, the flow through the outlet ports can maintain the high flow characteristics from the inlet port, but without the high pressure and resistance in the IV tubing attached to the catheter. In one aspect, the catheter can have 2-4 side outlet ports. The side outlet ports 78 can be oriented to face transverse to the longitudinal axis of the catheter. In addition, the side outlet ports 78 can be disposed around a circumference of the catheter. The side outlet ports can be circular or oval or oblong.

A sheath 82 can be affixed to the stylet 46, and removable with the stylet from the lumen. The sheath 82 can have a conical shape matching the conical internal shape 70 of the inner lumen conical taper of the catheter. Thus, the sheath 82 can cover the side outlet ports 78 when the stylet is completely inserted in the catheter. The sheath can be formed of plastic or stainless steel.

A method for high-volume peripheral intravenous (IV) introduction of a liquid into a vein, and for using the IV catheter described above, includes piercing a patient's skin and vein wall with a piercing tip 54 formed by a beveled distal end 50 of an elongate stylet 46. A distal end 26 of an elongate catheter 14 with an outlet port 30 through which the piercing tip of the stylet protrudes is advanced through the patient's skin and vein wall along the vein. As described above, the distal end 26 of the catheter 14 is relatively small (i.e. 20-27 gauge), and thus results in a little puncture to the skin (compared to a 14-18 gauge). Thus, the catheter hurts less to insert and is easier to insert into small veins. An inner lumen conical taper of the catheter is advanced through the patient's skin and vein wall along the vein to position a plurality of side outlet ports 78 formed laterally through the catheter in the inner lumen conical taper of the catheter in the vein with a proximal cylindrical shape 58 of the lumen extending from the distal tapered conical shape at a transition 62. The stylet is withdrawn from the lumen through an inlet port 22 at a proximal end 18 thereof. The plurality of distal side outlet ports can be uncovered by removing a sheath 82 affixed to the stylet, which sheath has a conical shape matching and covering the plurality of side outlet ports. Tubing or a syringe is coupled to a hub 34 at the inlet port of the catheter. A high velocity, high volume flow liquid is injected or introduced into the inlet port of the catheter. The liquid can include intravenous fluid, contrast dye, blood, a pharmaceutical compound, a saline solution, or mixtures thereof. The liquid flows through a larger interior diameter at the inlet port and a tapering smaller internal diameter between the transition and the outlet port, and out the plurality of side outlet ports and the outlet port with the same volume but lower pressure into the vein.

In addition, the high-volume peripheral IV catheter described herein can also be used to extract blood from the vein using standard phlebotomist techniques.

Example 1

An exemplary IV catheter in accordance with the above description was compared through computational fluid dynamics to other various catheter designs. The exemplary IV catheter had a 16 gauge (0.0403 inside diameter) inlet port, a 20 gauge (0.0253 inch inside diameter) outlet port, and four side outlet ports and a tapered configuration. The catheter was 2 inches long.

The exemplary IV catheter was compared to three other contrasting configurations for injecting or introducing a fluid. A first contrasting configuration is similar to the exemplary configuration, but without the side outlet ports. The second contrasting configuration was a straight 16 gauge (0.0403 inch inner diameter) catheter; while the third contrasting configuration was a straight 20 gauge (0.0253 inch inner diameter) catheter.

All four designs were subject to the same boundary conditions, i.e. outlet pressure, volumetric flow rate, laminar flow, fluid material, rigid wall, etc. All the catheters were the same length, i.e. 2 inches long. The volumetric flow rate was 5 cc/s and the outlet pressure was 80 mmHg (~10.7 kPa). The material was normal saline (0.9% NcCl) with a temperature of 21° C., a density of 1005 kg/m^3, a specific heat of 4182 J/kg-K, a thermal conductivity of 0.6 W/m-s, and a viscosity of 0.001003 kg/m-s. The inlet pressure, maximum stress and change in fluid velocity was calculated as follows in Table 1.

TABLE 1

| Design | Inlet Pressure (kPa) | Maximum Stress (kPa) | Change in Fluid Velocity (%) |
|---|---|---|---|
| Exemplary design with 16 gauge to 20 gauge taper and four side outlet ports | 44 | 136 @ outlet | 0 |
| First contrasting design with 16 gauge to 20 gauge taper, but no side outlet ports | 146 | 433 @ inlet | 150 |
| Second contrasting design with straight 16 gauge | 33 | 99 @ inlet | 4.7 |
| Third contrasting design with straight 20 gauge | 111 | 268 @ inlet | 10 |

From Table 1 it can be seen that the exemplary design compared to the contrasting design maintains the fluid flow (i.e. 0% change in fluid velocity). The exemplary design has similar characteristics for a straight 16 gauge catheter (i.e. second contrasting design), but with an ergonomic advantage in that the tip size is smaller for smaller veins. As noted above, smaller catheters, e.g. less than 20 gauge, results in IV tubing failure or splitting, as evidenced by the 20 gauge straight catheter (third contrasting design) with 268 kPa inlet pressure. Similarly, a tapering catheter without the side outlet ports (i.e. first contrasting design) might have similar tubing failure or splitting issues with 433 kPa at the inlet.

In addition, the exemplary IV catheter was compared to three other contrasting configurations for withdrawing a fluid, such as would be done to extract blood using standard phlebotomist techniques. The first through third contrasting configurations were as described above.

All four designs were subject to the same boundary conditions, i.e. outlet pressure equal to atmosphere, inlet pressure equivalent to central venous pressure, laminar flow, fluid material, rigid wall, etc. All the catheters were the same length, i.e. 2 inches long. The inlet pressure was 533 Pa (4 mmHg). The material was blood with a temperature of 37° C., a density of 1060 kg/m^3, and a viscosity of 0.0035 kg/m-s. The volumetric flow rate and the simulated time necessary to draw one pint of blood was calculated as follows in Table 2.

TABLE 2

| Design | Flow Rate (cc/s) | Time (min) |
|---|---|---|
| Exemplary design with 16 gauge to 20 gauge taper and four side outlet ports | 0.085 | 93 |
| First contrasting design with 16 gauge to 20 gauge taper, but no side outlet ports | 0.053 | 148 |
| Second contrasting design with straight 16 gauge | 0.084 | 94 |
| Third contrasting design with straight 20 gauge | 0.013 | 621 |

From Table 2 it can be seen that the exemplary configuration performs similar to that of a straight 16 gauge catheter (second contrasting design). Thus, even thought the exemplary design has a 20 gauge inlet port, the additional side inlet ports allow fluid to be withdrawn at the same rate as the 16 gauge catheter.

Figure 9:
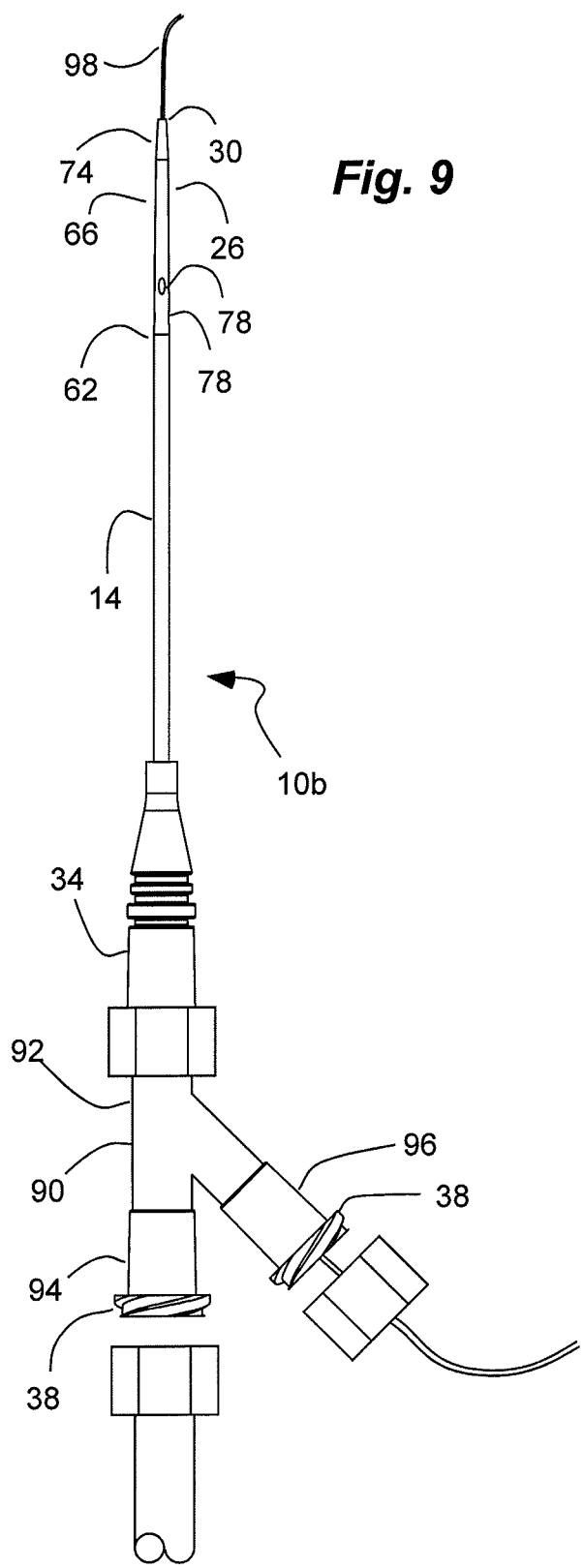
FIG. 9 is a side view of the peripheral IV catheter of FIG. 1 shown with a Y-connection and a double catheter configuration.

Referring to FIG. 9, another peripheral IV catheter 10b is shown that is similar in most respect to that described above, but with a Y-connection 90 and a double catheter configuration. The distal end 26 of the catheter 14 has the distal tapered conical shape 66 terminating at the outlet port 30 and defining the inner lumen conical taper with a conical internal shape. The Y-connection 90 can have one outlet 92 coupled to the hub 34, or connecter 38 thereof. In addition, the Y-connection 90 can have two inlets 94 and 96 which can be similar to the hub 34 and connecter 38. The outlet and inlets of the Y-connection can have a connector 38, such as a standard Luer lock connector, for connecting to syringes or tubing. One of the inlets can be utilized to introduce fluid into the patient's vein, as described above, while the other inlet can be utilized to introduce another fluid or device 98 into the patient's vein. For example, the device 98 can be a smaller secondary catheter floated by the main or primary catheter 14. The secondary catheter can have a size or diameter smaller than the primary catheter and can extend through the outlet port 30 of the main catheter. The side outlet ports 78 allow fluid to flow through the primary catheter even though the secondary catheter extends therethrough. The secondary catheter can infuse a medication that cannot be mixed with the fluid in the primary catheter. In addition, the secondary catheter can be used to draw blood from the patient's vein without stopping the IV infusion through the primary catheter. Thus, the secondary catheter can be a blood sampling catheter, a dug infusion catheter, etc. As another example, the device 98 can be a sensor for blood gas, sugar, venous pressure, oxygen saturation, temperature, etc., and combinations thereof. Thus, the sensor can be a temperature probe, SVO2 monitor, blood pressure monitor, etc. Such a sensor can replace a blood pressure cuff, mixed venous oxygen sensors, temperature monitors, etc. A distal end of the device 98, e.g. the secondary catheter or sensor, can extend through the outlet port 30 of the primary catheter 14, while the proximal end is coupled to tubing, a syringe, a monitor, etc.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A high-velocity, high-volume peripheral intravenous (IV) catheter device, comprising:
   a) an elongate flexible catheter with an elongate lumen therein, an inlet port at a proximal end, and an outlet port at a distal end opposite the inlet port;
   b) the lumen having a proximal cylindrical shape from the inlet port transitioning at a transition to an inner lumen conical taper, and having a larger internal diameter at the inlet port and a tapering smaller internal diameter between the transition and the outlet port;
   c) a plurality of side outlet ports formed laterally through the catheter nearer the transition than the outlet port;
   d) a cross-sectional area of the outlet port and the side outlet ports together being equal to or greater than a cross-sectional area of the inlet port;
   e) a hub disposed at the inlet port of the catheter;
   f) an elongate rigid stylet removably disposed in the lumen of the catheter and insertable and removable through the hub and the inlet port; and
   g) the stylet having a beveled distal end forming a piercing tip that protrudes from the outlet port of the catheter when the stylet is completely inserted in the catheter.

2. A device in accordance with claim 1, wherein:
   a) an inner diameter of the outlet port or an outer diameter of the stylet is approximately 23-27 gauge; and
   b) an inner diameter of the proximal cylindrical shape of the lumen of the catheter is approximately 16-18 gauge.

3. A device in accordance with claim 1, wherein the plurality of side outlet ports face transverse to a longitudinal axis of the catheter.

4. A device in accordance with claim 1, wherein the plurality of side outlet ports are disposed around a circumference of the catheter.

5. A device in accordance with claim 1, wherein the catheter is a primary catheter, the inlet port is a primary inlet, the outlet port is a primary outlet, and further comprising:
   the primary catheter having a secondary inlet; and
   a secondary catheter having a secondary outlet and insertable in the secondary inlet of the primary catheter, through the primary catheter, and out the primary outlet of the primary catheter with the stylet removed and with the secondary outlet of the secondary catheter beyond the primary outlet of the primary catheter.

6. A device in accordance with claim 1, wherein the inlet port is a primary inlet, and further comprising:
   the catheter having a secondary inlet; and
   a sensor insertable in the secondary inlet, through the catheter, and out the outlet port with the stylet removed.

7. A device in accordance with claim 1, wherein the catheter further includes:
   a primary outer taper corresponding to the inner lumen conical taper of the lumen;
   a secondary outer taper at a most distal end of the catheter with a wall thickness becoming thinner toward the most distal end; and
   the secondary outer taper being greater than the primary outer taper.

8. A device in accordance with claim 1, wherein the plurality of side outlet ports are formed laterally through the catheter between the transition and the outlet port.

9. A method for high-velocity and high-volume peripheral intravenous (IV) introduction of a liquid into a vein with a catheter device in accordance with claim 1, the method comprising:
   piercing a patient's skin and vein wall with the piercing tip of the elongate stylet completely inserted into the catheter;
   advancing the distal end of the catheter along with the stylet through the patient's skin and vein wall along the vein;
   advancing the inner lumen taper of the catheter through the patient's skin and vein wall along the vein to position the plurality of side outlet ports in the vein;
   withdrawing the stylet from the catheter;
   coupling tubing or a syringe to the hub at the inlet port of the catheter; and
   injecting a high velocity and high volume liquid into the inlet port of the catheter with the liquid flowing out the plurality of side outlet ports and the outlet port.

10. A method for extracting blood from a vein with a catheter device in accordance with claim 1, the method comprising:
   piercing a patient's skin and vein wall with the piercing tip of the elongate stylet completely inserted into the catheter;
   advancing the distal end of the catheter along with the stylet through the patient's skin and vein wall along the vein;
   advancing the inner lumen taper of the catheter through the patient's skin and vein wall along the vein to position the plurality of side outlet ports in the vein;
   withdrawing the stylet from the catheter; and
   extracting blood from the vein through the catheter.

11. A method for high-velocity, high-volume peripheral intravenous (IV) introduction of a liquid into a vein, comprising:
- piercing a patient's skin and vein wall with a piercing tip formed by a beveled distal end of an elongate rigid stylet;
- advancing a distal end of an elongate flexible catheter with an outlet port through which the piercing tip of the stylet protrudes through the patient's skin and vein wall along the vein;
- advancing an inner lumen taper of the catheter through the patient's skin and vein wall along the vein to position a plurality of side outlet ports formed laterally through the catheter in the vein;
- withdrawing the stylet from a lumen of the catheter through an inlet port at a proximal end thereof;
- coupling tubing or a syringe to a hub at the inlet port of the catheter; and
- injecting a high velocity and high volume liquid into the inlet port of the catheter with the liquid flowing through a larger interior diameter at the inlet port transitioning at a transition to a tapering smaller internal diameter between the transition and the outlet port and out the plurality of side outlet ports and the outlet port and into the vein at low pressure, with the side outlet ports and the outlet port having a cross-sectional area equal to or greater than a cross-sectional area of the inlet port.

12. A method in accordance with claim 11, wherein the liquid includes an intravenous fluid, contrast dye, blood, a pharmaceutical compound, a saline solution, or mixtures thereof.

13. A method in accordance with claim 11, wherein:
a) an inner diameter of the outlet port or an outer diameter of the stylet is approximately 23-27 gauge; and
b) an inner diameter of a proximal cylindrical shape of the lumen of the catheter is approximately 16-18 gauge.

14. A method in accordance with claim 11, wherein the plurality of side outlet ports face transverse to a longitudinal axis of the catheter.

15. A method in accordance with claim 11, wherein the plurality of side outlet ports are disposed around a circumference of the catheter.

16. A method in accordance with claim 11, wherein the catheter is a primary catheter, the inlet port is a primary inlet, the outlet port is a primary outlet, the primary catheter has a secondary inlet, and further comprising:
- inserting a secondary catheter with a secondary outlet in the secondary inlet of the primary catheter until the secondary outlet of the secondary catheter is beyond the primary outlet of the primary catheter.

17. A method in accordance with claim 11, wherein the inlet port is a primary inlet, the catheter has a secondary inlet, and further comprising:
- inserting a sensor in the secondary inlet of the catheter until the sensor is beyond the outlet port of the catheter.

18. A high-velocity, high-volume peripheral intravenous (IV) catheter device, comprising:
a) an elongate flexible catheter with an elongate lumen therein, an inlet port at a proximal end, and an outlet port at a distal end opposite the inlet port;
b) the lumen having a proximal substantially cylindrical shape from the inlet port transitioning at a transition to a distal tapered conical shape, and defining an inner lumen conical taper at the distal end of the lumen, and having a larger internal diameter at the inlet port and a tapering smaller internal diameter between the transition and the outlet port;
c) the larger internal diameter at the inlet port of the lumen being 16-18 gauge, a smaller internal diameter of the outlet port being 23-27 gauge;
d) a plurality of side outlet ports formed laterally through the catheter;
e) a cross-sectional area of the outlet port and the side outlet ports together being equal to or greater than a cross-sectional area of the inlet port;
f) a hub disposed at the inlet port of the catheter;
g) an elongate rigid stylet removably disposed in the lumen of the catheter and insertable and removable through the hub and the inlet port; and
h) the stylet having a beveled distal end forming a piercing tip that protrudes from the outlet port of the catheter when the stylet is completely inserted in the catheter.

19. A device in accordance with claim 18, wherein the plurality of side outlet ports are located closer to the transition than to the outlet port.

20. A device in accordance with claim 18, wherein the plurality of side outlet ports face transverse to a longitudinal axis of the catheter.

21. A device in accordance with claim 18, wherein the plurality of side outlet ports are disposed around a circumference of the catheter.

22. A device in accordance with claim 18, wherein the catheter is a primary catheter, the inlet port is a primary inlet, the outlet port is a primary outlet port, and further comprising:
- the primary catheter having a secondary inlet; and
- a secondary catheter having a secondary outlet port and insertable in the secondary inlet of the primary catheter, through the primary catheter, and out the primary outlet port of the primary catheter and with the secondary outlet port of the secondary catheter beyond the primary outlet port of the primary catheter.

23. A device in accordance with claim 18, wherein the inlet port is a primary inlet port, and further comprising:
- the catheter having a secondary inlet port; and
- a sensor insertable in the secondary inlet port, through the catheter, and out the outlet port.

24. A device in accordance with claim 18, wherein the catheter further includes:
- a primary outer taper corresponding to the distal tapered conical shape of the lumen;
- a secondary outer taper at a most distal end of the catheter with a wall thickness becoming thinner toward the most distal end; and
- the secondary outer taper being greater than the primary outer taper.

25. A method for high-velocity and high-volume peripheral intravenous (IV) introduction of a liquid into a vein with a catheter device in accordance with claim 18, the method comprising:
- piercing a patient's skin and vein wall with the piercing tip of the elongate stylet completely inserted into the catheter;
- advancing the distal end of the catheter along with the stylet through the patient's skin and vein wall along the vein;
- advancing the distal tapered conical shape of the catheter through the patient's skin and vein wall along the vein to position the plurality of side outlet ports and the outlet port in the vein;
- withdrawing the stylet from the catheter;
- coupling tubing or a syringe to the hub at the inlet port of the catheter; and injecting a high velocity and high volume liquid into the inlet port of the catheter with the liquid flowing out the plurality of side outlet ports and the outlet port.

* * * * *